United States Patent
Hyde et al.

(10) Patent No.: US 8,578,784 B2
(45) Date of Patent: Nov. 12, 2013

(54) SPECIMEN CREEP TEST AND METHODS OF USING SUCH TESTS

(75) Inventors: Thomas Horace Hyde, Nottingham (GB); Wei Sun, Nottingham (GB)

(73) Assignee: The University of Nottingham, Notinghamshire (GB)

( * ) Notice: Subject to any disclaimer, the term of this patent is extended or adjusted under 35 U.S.C. 154(b) by 122 days.

(21) Appl. No.: 13/130,247

(22) PCT Filed: Nov. 18, 2009

(86) PCT No.: PCT/GB2009/051560
§ 371 (c)(1),
(2), (4) Date: Jul. 27, 2011

(87) PCT Pub. No.: WO2010/058209
PCT Pub. Date: May 27, 2010

(65) Prior Publication Data
US 2011/0277553 A1    Nov. 17, 2011

(30) Foreign Application Priority Data
Nov. 19, 2008    (GB) .................................. 0821168.2

(51) Int. Cl.
*G01D 1/16*    (2006.01)

(52) U.S. Cl.
USPC ............................................. 73/789; 73/774

(58) Field of Classification Search
USPC ..................................... 73/760, 789, 774, 856
See application file for complete search history.

(56) References Cited

U.S. PATENT DOCUMENTS

| | | | |
|---|---|---|---|
| 3,599,476 A * | 8/1971 | Corbett | ........................... 374/50 |
| 3,693,419 A | 9/1972 | De Pierre et al. | |
| 3,842,664 A * | 10/1974 | Conway, Jr. | ..................... 73/760 |
| 4,821,577 A | 4/1989 | Thiercelin et al. | |
| 4,845,688 A * | 7/1989 | Butler | ........................... 367/174 |
| 5,495,772 A | 3/1996 | Dinzburg et al. | |
| 5,887,477 A * | 3/1999 | Newman | ........................ 73/159 |
| 5,974,871 A * | 11/1999 | Kanda et al. | ................ 73/114.78 |
| 6,595,068 B2 * | 7/2003 | Brovold et al. | .................. 73/803 |

(Continued)

FOREIGN PATENT DOCUMENTS

| | | |
|---|---|---|
| DE | 20 2004 020885 | 5/2006 |
| EP | 1 923 696 | 5/2008 |
| GB | 847 288 | 9/1960 |
| GB | 1 024 245 | 3/1966 |

OTHER PUBLICATIONS

Horide et al., "Characterization of Fracture Process during Ring Burst Test of FW-FRP Composites with Damage", Adv. Composite Mater., 8(2):139-151 (1999).

Hyde et al., "A novel, high sensitivity, small specimen creep test", J. Strain Analysis, 44:1-15 (2009).

(Continued)

*Primary Examiner* — Max Noori
(74) *Attorney, Agent, or Firm* — Fennemore Craig, P.C.

(57) ABSTRACT

A method for testing the mechanical properties of a specimen. The specimen is generally characterized by a first contact surface and a second contact surface spaced apart from and opposing the first contact surface. The method involves applying forces to the contact surfaces of the specimen to deform the specimen over a period of time. The response of the specimen to the forces is then measured over time. A spatial distance between the contact surfaces is defined such that the equivalent gauge length of the specimen is greater than the distance between the contact surfaces.

34 Claims, 10 Drawing Sheets

(56) References Cited

U.S. PATENT DOCUMENTS

| | | | |
|---|---|---|---|
| 6,655,192 B2 * | 12/2003 | Chavdar | 73/38 |
| 6,810,748 B1 | 11/2004 | Nishida et al. | |
| 7,252,012 B2 * | 8/2007 | Kim | 73/803 |
| 2006/0070455 A1 | 4/2006 | Hendrich et al. | |

OTHER PUBLICATIONS

International Search Report and Written Opinion for PCT/GB2009/051560 dated Mar. 19, 2010.

Great Britain Search Report for GB0821168.2 dated Mar. 17, 2009.

* cited by examiner (a) Displacement Δ measured due to a given force P.

(b) Rotation ω measured due to a pure moment M.

(c)

(d)

(e)

(f)

(g)

(h)

(i)

(j)

(k)

SPECIMEN CREEP TEST AND METHODS OF USING SUCH TESTS

RELATED APPLICATION DATA

This application is the U.S. national stage of PCT/GB2009/051560 filed Nov. 18, 2009, which claims priority to and benefit of Great Britain Patent Application No. 0821168.2 filed Nov. 19, 2008, the contents of each of which are herein incorporated by reference for all purposes.

FIELD OF THE INVENTION

This invention relates to a novel specimen type and the associated method for testing the mechanical properties of a material, and in particular, but not exclusively for accurately obtaining creep strain data for a sample of material which is relatively small in size.

BACKGROUND OF THE INVENTION

Materials such as metal can creep if they experience stress at a high enough temperature, over a long period of time. One of the primary aims of a designer of equipment operating in a creep range is to plan for the possibilities of failure by excessive deformation and avoid such failure. For example, dimensional changes with time, even of the order of a few millimetres, leading to mismatch of components or contact between moving parts, could lead to serious damage to plant, not to mention loss of human life and revenue.

Therefore there is a need for the generation of ways of predicting whether components operating in the creep range will sustain the life required of them. The useful life of a material could be terminated when deformation becomes excessive, when rupture occurs or when latent flaws or initiated cracks grow at unacceptable rates by creep or creep/fatigue.

Creep is defined as a high temperature progressive deformation at constant stress. "High temperature" is a relative term dependent upon the materials involved. Creep rates are used in evaluating materials for boilers, gas turbines, jet engines, ovens, or any application that involves high temperatures under load. Understanding high temperature behaviour of metals is useful in designing failure resistant systems.

Conventional uniaxial creep tests using cylindrical bar type specimens are usually performed for determining the creep properties. Creep occurs in three stages: Primary, or Stage I; Secondary, or Stage II: and Tertiary, or Stage III. Stage I, or Primary creep occurs at the beginning of a components life during which the strain rate reduces. Resistance to creep increases until Stage II is reached. In Stage II, or Secondary creep, the rate of creep becomes roughly steady. This stage is often referred to as steady state creep. In Stage III, or tertiary creep, the creep rate begins to accelerate as the cross sectional area of the specimen decreases due to (i) material degradation, and (ii) necking or internal voiding which decreases the effective area of the specimen. If stage III is allowed to proceed, fracture will occur.

Creep tests are usually employed to determine the minimum creep rate in Stage II. Engineers need to account for this expected deformation when designing systems. Currently there are three types of tests commonly used to determine creep strain data for a sample of material which is relatively small in size. These are the uniaxial, impression and small punch tests which are described further below.

To determine creep properties from the uniaxial creep test using small uniaxial specimen, material is subjected to prolonged constant tension or compression loading at constant temperature. Deformation is recorded at specified time intervals and a creep strain vs. time diagram is plotted. Slope of curve at any point is creep rate. If failure occurs, it terminates the test and Time for Rupture is recorded.

Impression creep testing, wherein a flat-ended cylindrical punch is used to load a small area of the specimen in compression, enables testing of small material volumes and the use of miniaturized specimens, with minimal preparation. However, under very slow creeping situations (depending on material, stress and temperature), a considerable time is necessary for the evolution of a steady-state creep zone under the punch, resulting in a prolonged period of decreasing creep rate even when the constitutive creep behaviour is strain-independent. This test-dependent transient behaviour, where the creep rate decreases slowly even at very long test times, complicates the determination of true material creep parameters. The very small creep deformations which occur under such conditions can be very difficult to accurately measure.

Small punch creep (SPC) test technique is another method used to evaluate the creep properties of materials extracted from components in a high temperature environment. The SPC uses a number of theory and test techniques for the purpose of applying the SPC test to the residual creep life assessment of plant components. However, as it is carried out in a high temperature environment using very thin miniature disc specimens, which is different from conventional uniaxial creep tests described above. The creep properties of the test specimens can be significantly influenced by surface oxidation. Moreover, when creep and oxidation occur simultaneously, it becomes difficult to unambiguously distinguish which changes are attributable to oxidation and which to fracture. When the oxide is strong and firmly adherent to the metal, it can improve creep strength, but if the oxide had low inherent strength or spalls away from the surface, creep strength can decrease.

The advantage that the small punch test method has relative to the impression creep test method is that it involves tertiary creep and fracture, whereas the impression creep test method only gives information on secondary creep behaviour and some indication about primary creep. However, so far the small punch test method does not have a fully verified and universal route for interpreting the primary, secondary and tertiary contributions to the overall displacement versus time curve.

For practical small specimen dimensions, the "test section" area for all three specimen types can be made large enough to enable "bulk" creep properties to be obtained (as opposed to single grains, or a few grain boundary properties being determined, which can be the case if the sample is very small). Similarly, all three have relatively small equivalent gauge length (EGLs), i.e. 2 to 10 mm for practical dimensions. The term EGL is defined as the length by which the measured deformation must be divided to give the equivalent strain to that which would be obtained from a corresponding uniaxial test.

The term "gauge length" is used in mechanical testing, it is the length, usually marked on a portion of a tensile test piece over which the elongation is measured.

In order to obtain results in reasonably short timescales (tests are usually carried out for times in the range 500 h to 3000 h), and in order to get easily measureable deformations with high accuracy, tests are often conducted at relatively high "stress" levels and/or temperatures, as compared with typical values of stress and temperature that a component would be designed to endure. All three specimen types currently being used are relatively "stiff" and so there is little scope for significantly increasing the EGL.

Any discussion of documents, acts or knowledge in this specification is included to explain the context of the invention. It should not be taken as an admission that any of the material forms part of the prior art base or the common general knowledge in the relevant art.

SUMMARY OF THE INVENTION

According to a first aspect, the present invention provides a method for testing the mechanical properties of a specimen having a first contact surface and a second contact surface spaced apart and opposing the first contact surface, the method comprising: applying forces to the contact surfaces of the specimen to deform the specimen over a period of time and determining the response of the specimen to the forces over time; and defining a spatial distance between the contact surfaces such that the equivalent gauge length of the specimen is greater than the distance between the contact surfaces.

The method may further comprise obtaining a sample of material from an object to be tested and forming the specimen from the sample or operating on the sample with machine tools to form the specimen or forming a ring-like shaped specimen from the sample. The first contact surface may be either a concave surface or convex surface, and wherein the second contact surface is also either a concave surface or a convex surface. The specimen may be symmetrical about a line joining the contact surfaces. The specimen may comprise an elliptical shape or a circular shape. The specimen may have a flattened elliptical shape having two opposed generally parallel sides and at least one, and preferably two, curved regions linking the parallel sides. The forces that may be applied to the contact surfaces forces the surfaces toward each other. The forces that may be applied to the contact surfaces forces the surfaces away from each other. The forces applied to the contact surfaces may be a diametric force which causes the contact surfaces to deform diametrically as a result of the forces being applied to at least a point on the contact surfaces. The diametric force may be either a tension force or a compression force applied to the contact surfaces. The equivalent gauge length of the specimen may be significantly greater than the distance between the contact surfaces. The equivalent gauge length of the specimen may be greater than or equal to 20 mm. The equivalent gauge length of the specimen may be at least two times or four times the distance between the contact surfaces. The method may further comprise heating the specimen to a temperature which may be substantially the same as the operating temperature which the sample made from the material would operate at. The specimen may be formed from a sample by a sample scooping technique or any other specimen retrieval technique. A force may be applied to either the first contact surface or the second contact surface and the other contact surface which does not have the force applied to it is secured to an apparatus for testing the mechanical properties of the specimen, wherein when the force is applied to the first surface or the second contact surface an equal and opposite reactive force is applied to the other contact surface. The first contact surface and/or the second contact surface may be shaped so as to self-align or self-centre a specimen within the apparatus for testing the mechanical properties of the specimen. The first contact surface and/or the second contact surface may be shaped so as to self-align or self-centre a specimen within the apparatus for testing the mechanical properties of the specimen. The method may further comprises hanging a weight from either the first contact surface or the second contact surface and using the other contact surface which does not have the weight applied to it to react to the force of the weight. Testing the mechanical properties of the specimen may comprise creep testing the specimen.

According to a further aspect, the present invention provides a specimen for testing the mechanical properties of a material, the specimen comprising: a first contact surface; a second contact surface; wherein the second contact surface opposes the first contact surface and defines an opening in between each surface; and wherein the specimen defines a spatial distance between the contact surfaces such that the equivalent gauge length of the specimen is greater than the distance between the contact surfaces.

The first contact surface may be either a concave surface or convex surface, and wherein the second contact surface is also either a concave surface or a convex surface. The specimen may be symmetrical about a line joining the contact surfaces. The specimen may comprise a ring-like shape. The specimen may comprise an elliptical shape, or a flattened elliptical shape, or a circular shape, or a split-ring shape, or a C-shape, or the like. The specimen may be formed from a sample of the material by a sample scooping technique or any other specimen retrieval technique. The equivalent gauge length of the specimen may be significantly greater than the distance between the contact surfaces. The equivalent gauge length of the specimen may be greater than or equal to 20 mm. The equivalent gauge length of the specimen may be at least two times or four times the distance between the contact surfaces. A force may be applied to either the first contact surface or the second contact surface and the other contact surface which does not have the force applied to it is secured to an apparatus for testing the mechanical properties of the specimen, wherein when the force is applied to the first surface or the second contact surface an equal and opposite reactive force is applied to the other contact surface. The first contact surface and/or the second contact surface may be shaped so as to self-align or self-centre a specimen within the apparatus for testing the mechanical properties of the specimen. The specimen may further comprise hanging a weight from either the first contact surface or the second contact surface and using the other contact surface which does not have the weight applied to it to react to the force of the weight. Testing the mechanical properties of the specimen may comprise creep testing the specimen.

According to a still further aspect, the present invention provides an apparatus for testing the mechanical properties of a material to determine a creep characteristic of a sample taken from the material, the sample comprising a first contact surface, a second contact surface spaced apart and opposing the first contact surface, applying forces to the contact surfaces of the sample to deform the sample over a period of time, and the sample defines a gap between the contact surfaces such that the effective gauge length of the sample is greater than the distance between the control surfaces, the apparatus comprising: an apparatus to apply the forces to the contact surfaces to deform the sample over a period of time; a heating device to heat the sample; and a processor to calculate a steady state time dependent deformation rate to determine a creep strain rate.

According to a still further aspect, the present invention provides a method of forming a sample from a material, the sample being used for testing the mechanical properties of the material, the method comprising: extracting the sample from the material; forming the sample into a test specimen having a first contact surface, a second contact surface spaced apart and opposing the first contact surface; applying forces to the contact surfaces of the specimen to deform the specimen over a period of time and determining the response of the specimen to the forces over time; and defining a spatial distance between the contact surfaces such that the equivalent gauge length of the specimen is greater than the distance between the contact surfaces.

According to a still further aspect, the present invention provides a process for producing a product from a production plant comprising: operating the plant to produce the product; checking the expected operational life of a component of the plant by: (i) obtaining a sample of the material of a component of the plant, and forming from the sample a specimen in accordance with any one of claims 21 to 29; (ii) performing a creep test on the specimen using the method according to any one of claims 1 to 20; determining that the component has a remaining safe operational life; and continuing to produce more product, using the component in the future.

The product may be electricity and the plant may be an electricity generating plant.

The present invention overcomes or reduces the problems associated with the prior art by producing a specimen type which makes the specimen relatively "flexible" and hence relatively larger deformations are measured and used to produce relatively low creep strain data equivalent to relatively low equivalent uniaxial data related to stress levels. It is of course easier to measure larger deformations, and the test can be performed faster at lower temperatures.

The most important aspect of the small sample design concept within this invention is the high EGL values which can be achieved. This allows easily measureable deformations to be obtained related to relatively small strains. Hence, apart from the ease with which the experiments can be performed, stresses and temperatures can be chosen to be much closer to practical operating values; most small specimen creep testing which is carried out is performed at elevated stress and/or temperature.

The various features of novelty which characterize the present invention are pointed out with particularity in the claims annexed to and forming part of this disclosure. For a better understanding of the present invention, its operation, advantages and specific objects attained by its use, reference should be had to the accompanying drawings and descriptive matter in which preferred embodiments of the invention are illustrated and described.

DESCRIPTION OF PREFERRED EMBODIMENT

The present invention will be discussed hereinafter in detail in terms of the preferred embodiment of a novel specimen type and associated method of testing a sample from an object to determine the mechanical properties and in particular for testing and obtaining creep strain data. In the following description, numerous specific details are set forth in order to provide a thorough understanding of the present invention. It will be obvious, however, to those skilled in the art that the present invention may be practiced without these specific details.

Figure 1:
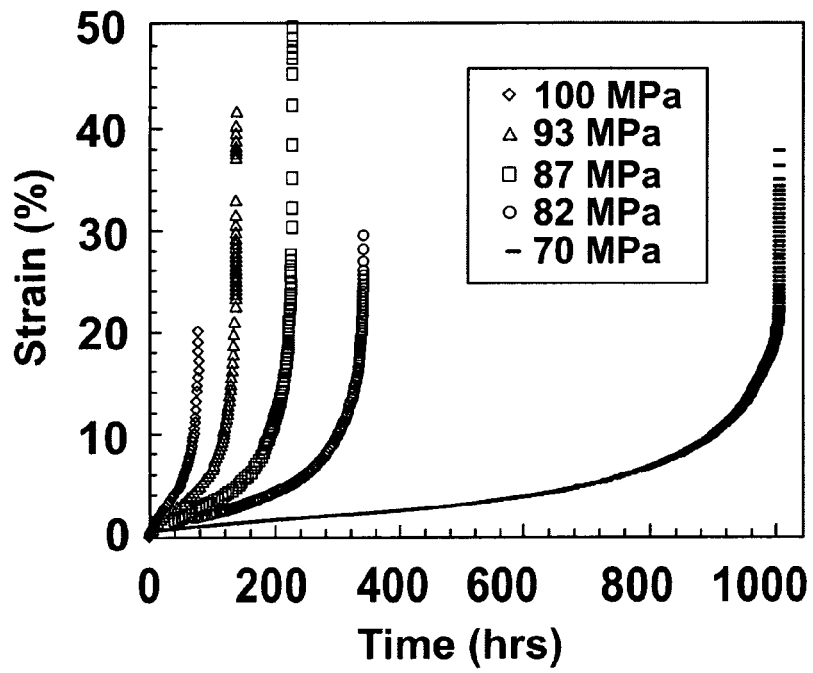
FIG. 1 shows a graph of creep curves produced by using uniaxial specimens according to the prior art.

Many components and structures in, for example, power plant or an electricity generating plant, chemical plant, aero engines, super-plastic forming dies etc, operate at temperatures high enough for creep to occur. In order to predict the creep behaviour of these components, "bulk material creep properties" are required. Typical, "bulk property" creep curves are shown in FIG. 1; these curves include primary (reducing strain rate) creep during the early stages followed by relatively steady strain rates in the secondary region, leading to tertiary creep and finally to fracture. The test used in this case was the uniaxial creep test for P91 steel at 650° C.

In order to produce a sample a technique known as scooping using a hemispherical shaped toothed saw type cutter powered by an air motor is used. The cutting surface is lubricated and cooled using a water mist system with a high temperature lubricant. The cooling system prevents sparks, allowing the device to cut the small samples from such equipment as power plant, chemical plant, aero engines, super-plastic forming dies etc, which operate at temperatures high enough for creep to occur. Obviously other techniques for producing the sample can be used without departing from the scope of the invention. The present invention can be used to obtain data corresponding to that shown in FIG. 1 for small samples of material. The small samples can be of new material or of pieces of material extracted from components (which may be service aged) using for example the scoop technique. A small sample is taken to be typically of the order of a few mm in size and a few grams in weight.

Figure 3:
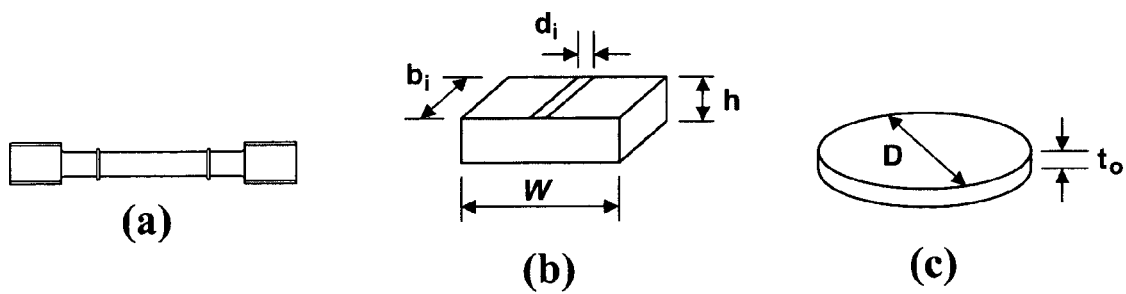
FIG. 3 shows the typical shapes used for small specimen type creep tests according to the prior art.
Figure 6:
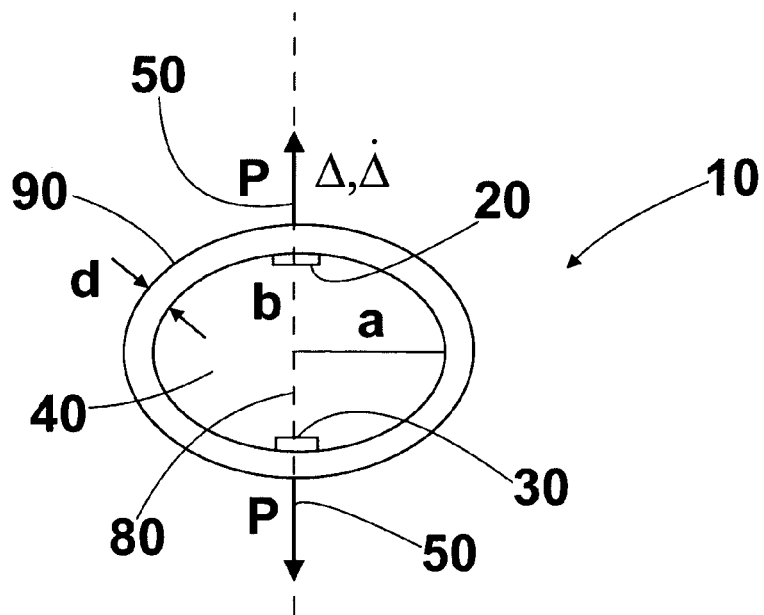
FIG. 6 shows a plan view of a diametrically loaded ring in accordance with a preferred embodiment of the present invention.

Specimens such as those shown in FIG. 3 and FIG. 6 are machined from the samples "scooped" from the components. The test machines loading apparatus, temperature and deformation control systems etc, used for the tests are the same or similar to those which would be used for small uniaxial, impression and small punch tests.

Figure 2:
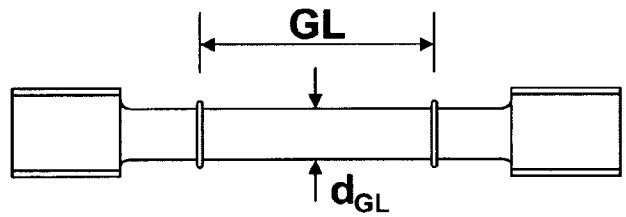
FIG. 2 shows a typical uniaxial specimen which would have been used to produce the graph of FIG. 1.

FIGS. 2 to 5 show the current practice used for small specimen creep tests available in order for engineers to predict whether components operating in the creep range will sustain the life required of them. As described above there are three test methods currently available to determine creep strain data from small samples, they are: (a) Uniaxial creep test; (b) Impression creep testing: and (c) Small punch creep test. All three tests use small specimens of material as shown in FIGS. 2 and 3.

FIG. 3(a) shows small diameter specimens, typically 1.5 to 3 mm in diameter which may be electron beam welded into conventional end pieces. Tests were carried out in inert atmospheres and specialised loading frames were used to accommodate the low loads required. Data were obtained for four materials (0.5Cr0.5Mo0.25V, 1Cr0.5Mo, 1.25Cr0.5Mo and 2.25Cr1Mo) and results were compared with those of conventional creep tests. Provided grain sizes are not too large, specimen diameters as small as 1 mm can be used to produce "bulk" material creep properties. Small gauge lengths (<10 mm) can significantly reduce strain measurement sensitivities compared to conventional creep test specimens and can make strain measurements sensitive to relatively small temperature variations. The effects of specimen misalignment are greater when specimen diameters are small. In addition specimen manufacture is more complicated and more expensive than for conventional "full size" specimens.

Figure 4:
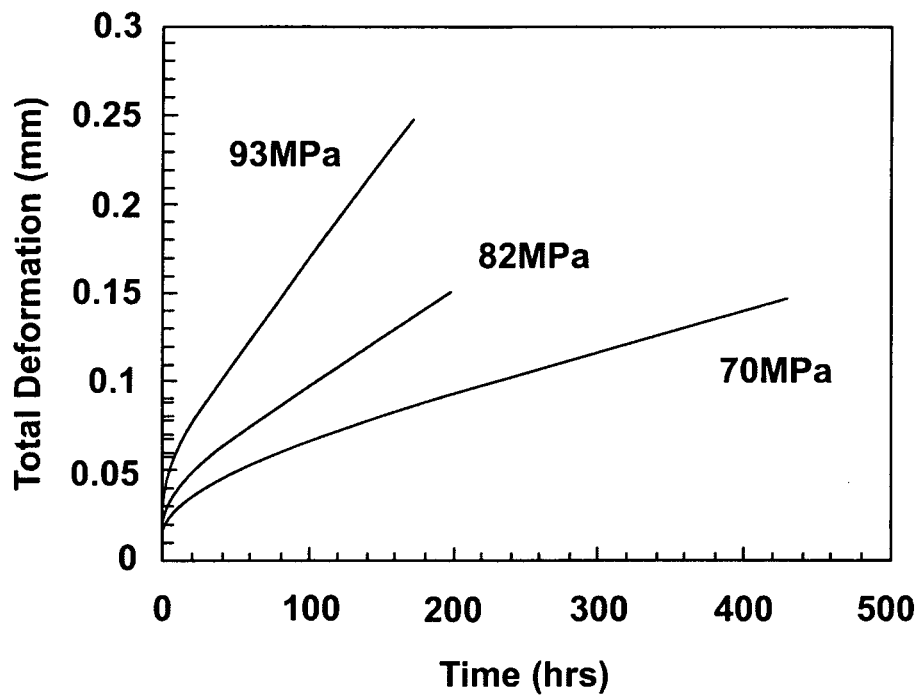
FIGS. 4 and 5 show graphs of creep curves for both the impression test and the small punch test respectively according to the prior art.

FIG. 3(b) shows a typical small specimen used in an impression creep test. In this case the dimensions of the block are; width=$b_i$ is approximately 10 mm with a height of approximately 2.5 mm and having an impression width=$d_i$ of approximately 1 mm. The technique has been used for a wide range of materials (e.g. low alloy ferritic CrMoV steels, stainless steels, high chromium martensitic steels such as P91 and T91). A typical set of data obtained from such tests is shown in FIG. 4. The corresponding equivalent uniaxial stress, σ, and creep strain, $\epsilon^c$, are related to the mean indenter pressure, $\bar{p}$, and impression creep displacement, $\Delta^c$, via relationships:

$$\sigma = \eta \bar{p} \text{ and} \tag{1}$$

$$\varepsilon^c = \frac{\Delta^c}{\beta d_i} \tag{2}$$

The η and β values for the recommended specimen geometry (10 mm×10 mm×2.5 mm) are η=0.430 and β=2.18. These are independent of material properties and do not vary with impression depth provided $\Delta^c$ is relatively small compared to the specimen thickness, h.

The area of contact (10 mm×1.0 mm) will generally be large compared to metallurgical features and hence the test is capable of producing "bulk" material creep properties. The quantity "$\beta d_i$" in equation (2), is divided into the measured displacement, $\Delta^c$, to obtain the creep strain. Hence, $\beta d_i$ can be thought of as being the equivalent gauge length (EGL) for the corresponding uniaxial creep test carried out at a stress level of η$\bar{p}$. Therefore, for strain sensitivity considerations the EGL of the recommended specimen geometry is about 2 mm (=$\beta d_i$). This is of similar magnitude to that for a typical, conventional, sub-size specimen.

Figure 5:
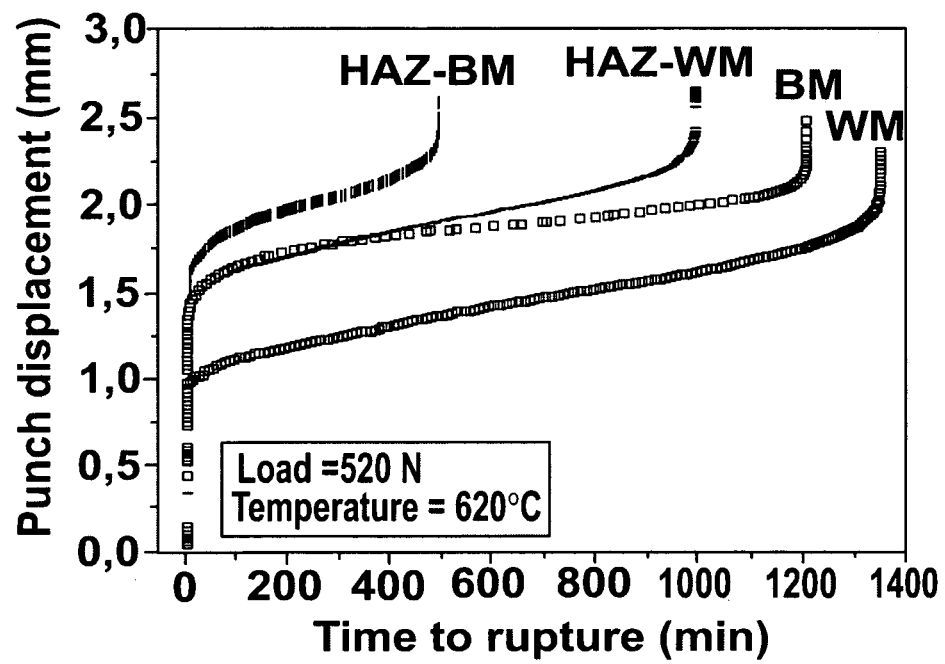

FIG. 3(c) shows a typical small specimen used in the small punch creep (SPC) test. Typical specimen dimensions measure approximately 8 mm in diameter and 0.5 mm in thickness. The small punch test involves large deformations relative to the specimen thickness. Test data obtained from this type of test is shown in FIG. 5. FIG. 5 shows that there are two distinct zones for the punch displacement which occurs during a test. First, there is a zone related to dishing of the supporting edge, which is significant during the early stages of a test. This is followed by necking near the edge of the contact zone. This behaviour may be predicted by the Chakrabarty membrane stretch model.

The failure location in small punch creep tests is near the edge of contact between the punch and the specimen. Based on the Chakrabarty membrane theory, expressions have been determined relating the strain at the edge of contact position to the displacement. Similarly, the ratio of the force to membrane stress, P/σ, and the displacement have been determined. For the case of $a_p$=2.0 mm and $R_s$=1.25 mm, the P/σ ratio and edge of contact strain, ε, for Δ>0.8 mm, are given by:—

$$P/\sigma = 1.72476\Delta - 0.05638\Delta^2 - 0.17688\Delta^3 \tag{3a}$$

$$\epsilon = 0.17959\Delta + 0.09357\Delta^2 + 0.00440\Delta^3 \tag{3b}$$

The maximum P/σ value, based on the Chakrabarty membrane theory is 1.89, when Δ=1.6 mm. When Δ>1.6 mm, P/σ decreases because of the thickness reduction which occurs.

The variation of the maximum P/σ, with $a_p$, $R_s$, and $t_o$, for Δ>0.8 mm, has been obtained and this leads to an expression for a of the form:—

$$\sigma = \frac{0.3}{K_s} \frac{P a_p^{0.2}}{R_s^{1.2} t_o} \tag{4}$$

where P is the small punch load and $a_p$, $R_s$, and $t_o$ are the radius of the disc between the supports, radius of the punch and initial thickness of the disc, respectively; $K_s$ is a correlation factor, which is determined empirically for the particular material.

By using equation (3b) the deflection versus time curves obtained experimentally can be converted to strain versus time curves. Similarly, the variation of P/σ (and hence σ) can be obtained by using equation (3a). Hence, the stationary strain rates can be obtained from the secondary stages of the creep tests.

FIG. 6 shows an embodiment of the present invention of a method for testing the mechanical properties of an object. Typically an object may be a component or a structure, from for example, a power plant, a chemical plant, aero engines, super-plastic forming dies, boilers etc, which operate at temperatures high enough for creep to occur. As was described above a blank is taken from the object by a suitable method. One such suitable method, being a scooping technique which is used to produce a scoop sample using a hemispherical shaped toothed saw type cutter powered by an air driven motor. Obviously other known methods of producing a sample which are known may be used. For example the tubes which are produced as part of the deep hole drilling method, for obtaining residual stresses, can be used.

The sample 10 which is machined (or otherwise extracted) from the blank has two contact surfaces, a first contact surface 20 and a second contact surface 30. The second contact surface 30 being spaced apart and opposing the first contact surface 20 and defining an opening 40 between the two contact surfaces. The contact surfaces 20, 30 may be either concave surfaces or convex surfaces. The contact surfaces 20, 30 may also be symmetrical about a line 80 joining the contact surfaces. For example the sample 10 may be a ring like object (or similar flexible specimen such as a spring), either a circular ring 100 or an elliptical ring 90. However, any ring like (or similarly flexible) shape may be used without departing from the scope of the present invention. The sample 10 used for determining creep in an object or solid material may be for example a small sample 10 which may be defined as a sample, typically 10 mm in diameter (ie b=10 mm) with a radial thickness, d, of approximately 0.5 mm and a length in the z direction of 2 mm which is capable of being deformed.

Figure 16:
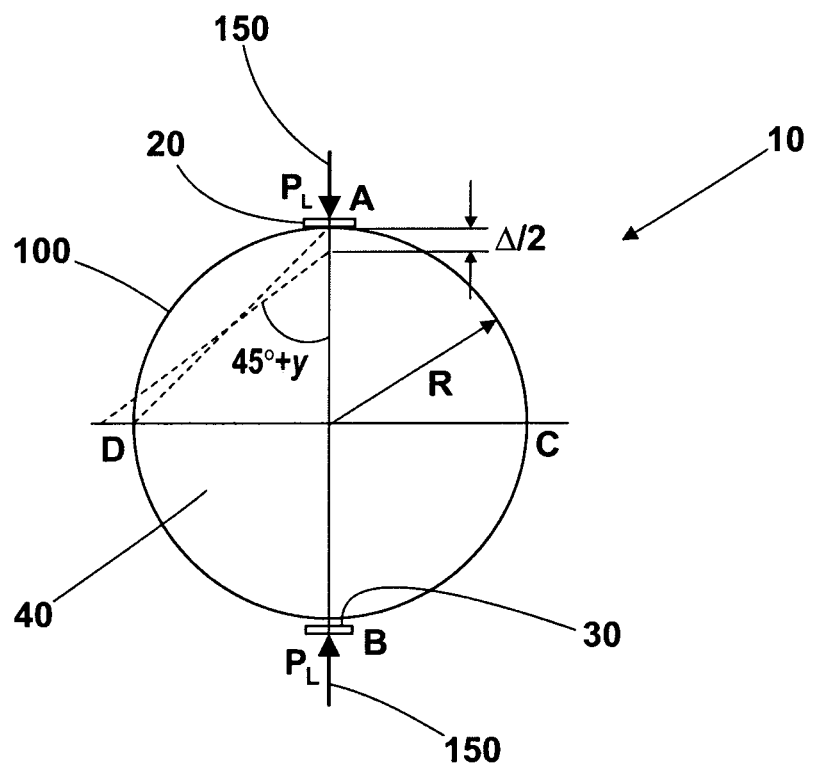
FIG. 16 shows a diagram of the load and deformation of the ring with fully plastic hinges at positions A, B, C and D which are used for an approximate analytical solution in accordance with the present invention.
Figure 17:
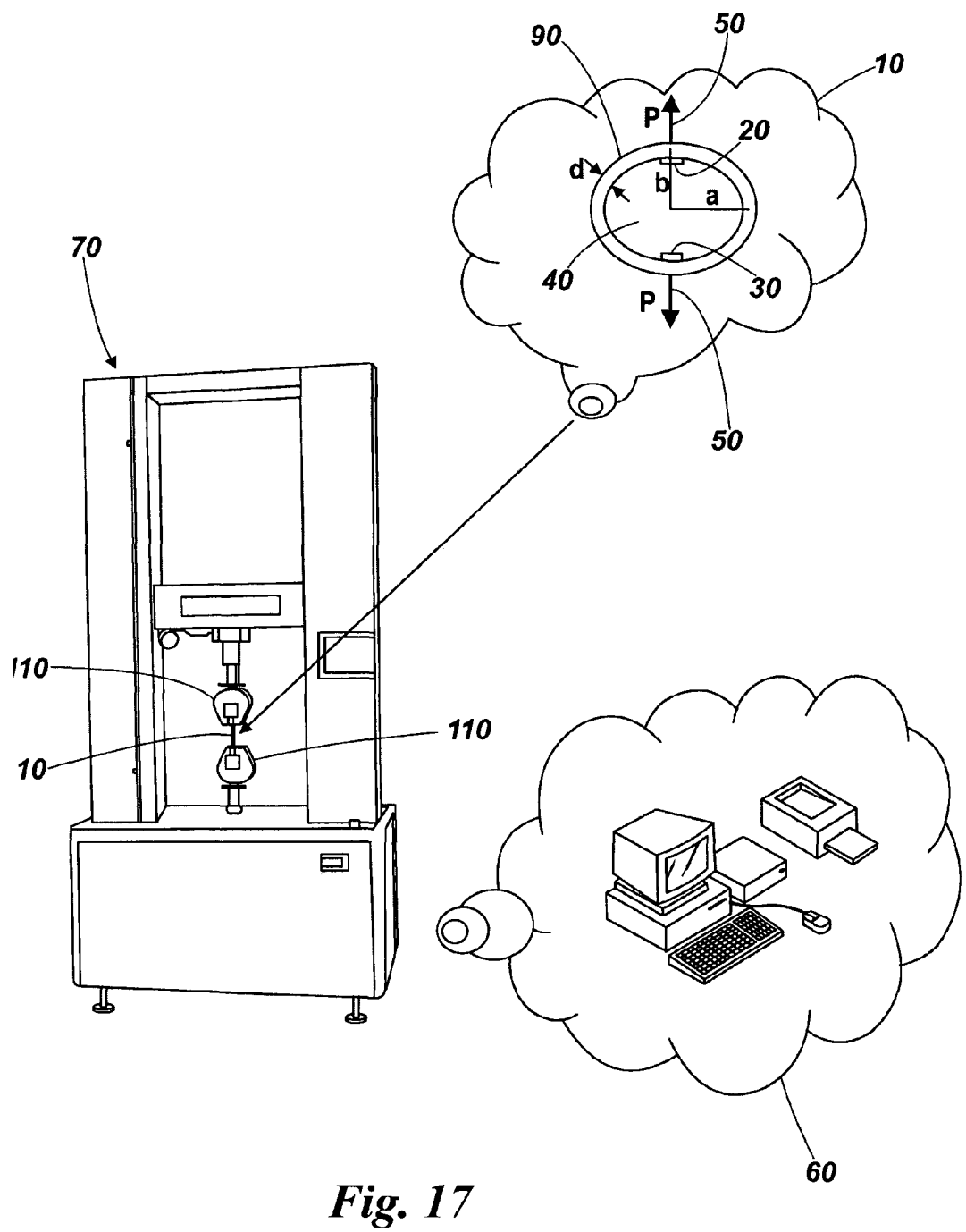
FIG. 17 shows an apparatus for testing the mechanical properties of an object in accordance with the present invention.

In order to test a sample 10 from an object to determine the mechanical properties and in particular for testing and obtaining creep strain data, the sample 10 requires a force to be applied to the contact surfaces 20, 30 of the sample 10 to deform the sample over a period of time. FIG. 17 shows a typical test apparatus for determining the mechanical properties of a sample 10 in accordance with the present invention. The apparatus consists of a uniaxial tension device 70 with upper and lower clamping members 110. The sample 10 is placed between the contacting members 110 and a tension force is applied at the contact surfaces 20, 30 in the direction of points (P) 50 on the sample 10. It is also possible to use a compression force and is illustrated in FIG. 16 using a circular ring 100. The compression force is applied at the contact surfaces 20, 30 in the direction of points (P) 150 on the sample 10. In the above example the elliptical ring 90 having a first contact surface 20 and a second contact surface 30 is placed between the contacting members 110 and a tension force is applied at points 50 on the elliptical ring 90. Due to the sample 10 being placed between the contacting members 110 the process of self centering of the sample 10 is achieved. It is also possible to test for other mechanical properties, for example yield stress which is the stress at which yield occurs being dependent on both the rate of deformation (strain rate) and, more significantly, the temperature at which the deformation occurs, and d-plastic stress-strain curves being the graphical measure of a material's mechanical properties.

A computer 60 or similar processor controls the uniaxial tension device 70 and is also used to calculate a steady state time dependent deformation rate to determine a creep strain rate, the creep strain rate is dependent upon the relationship of the deformation and an effective gauge length of the sample 10. The apparatus also includes a heating device (not shown) for example a heating element or furnace controlled by a thermocouple or similar device. The sample 10 is heated to a temperature substantially the same as the operating temperature of the object from which the sample 10 is taken.

The object of the uniaxial creep test is to find the steel properties equivalent to those which would be obtained from a test case out in a state of pure tensile stress. The device 70 loads a test specimen 10 and records the load vs. deflection.

The compressive loading may also be used in which the sample 10 is compressed rather than stretched. In this embodiment the ring like shape is used. The ring like shape has a force applied to the contact surfaces which may either force the contact surfaces towards each other or away from each other depending on whether a tension or compression test is used. Due to the shape of the ring like sample a diametric force may be applied which causes the contact surfaces to deform diametrically. Further the diametric force may be either a tension or compression force applied to the contact surfaces. In this embodiment the diametrically loaded sample, in this case an elliptical ring 90, as shown in FIG. 6, can be loaded in tension or compression. It is designed to be flexible to enable small strains to be related to relatively large deformations.

Another aspect of the sample design concept is the high equivalent gauge length (EGL) values which can be achieved. This allows easily measureable deformations to be obtained related to relatively small strains. Hence, apart from the ease with which the experiments can be performed, stresses and temperatures can be chosen to be much closer to practical operating values. As stated above the term "gauge length" is used in the mechanical testing of materials, it is the length marked on a portion of a tensile test piece 10 over which the elongation is measured. Therefore, the EGL means the length which must be divided into the measured deformation of the specimen 10 in order to obtain the strain equivalent to that which would be obtained in a creep uniaxial tensile test.

In this embodiment the sample defines a gap 40 between the contact surfaces 20, 30 such that the equivalent gauge length of the sample 10 is greater than the distance between the contact surfaces 20, 30. This embodiment of the present invention overcomes the problems associated with the prior art by producing a sample which is relatively "flexible" and hence larger deformations are measured and used to produce relatively low creep strain data related to relatively low equivalent uniaxial stress levels. The equivalent gauge length may be very large by comparison with the specimen dimensions (in particular the distance between the points between which the deformation is measured). Typically the equivalent gauge length can be of the order of at least four times the distance between the points between which the deformation is measured. It is relatively easy to have an EGL of at least 50 mm for a sample according to the present invention. By way of example, from table 1 below, for a circular ring with R=6 mm, $\beta=0.448$ and d=1 mm and using the formula for effective gauge length;

$$EGL = \frac{4R^2\beta}{d}$$

An equivalent gauge length of approximately 65 mm may be achieved.

| Geometry (FIG) | $\sigma_{nom}$ | $\eta$ | $\beta$ | EGL ($\beta l$) | Test Area | Typical Dimensions |
|---|---|---|---|---|---|---|
| Uniaxial (3(a)) | $\dfrac{4P}{\pi d_{GL}^2}$ | 1 | 1 | 1 | $\dfrac{\pi d_{GL}^2}{4}$ | l < 10 mm<br>$d_{GL}$ < 3 mm |
| Impression (3(b)) | $\dfrac{P}{b_i d_i}$ | ~0.4 | ~2.0 | ~$2d_i$ | $b_i d_i$ | $b_i$~1 mm<br>$d_i$~10 mm<br>h~2.5 mm |

-continued

| Geometry (FIG) | $\sigma_{nom}$ | $\eta$ | $\beta$ | EGL ($\beta l$) | Test Area | Typical Dimensions |
|---|---|---|---|---|---|---|
| Small Punch (3(c)) | $\dfrac{P}{2\pi R_s t_o}$ | $\dfrac{0.6\pi}{K_s}\left(\dfrac{a_p}{R_s}\right)^{0.2}$ | — | — | $2\pi R_s t_o$ | $R_s \sim 1.25$ mm<br>$t_o \sim 0.5$ mm |
| Circular Ring | $\dfrac{PR}{b_o d^2}$ | 0.892 | 0.448 | $\dfrac{4R^2\beta}{d}$ | $2b_o d$ | R = 6 mm<br>$b_o$ = 2 mm<br>d = 1 mm |
| Elliptical Ring (6) | $\dfrac{Pa}{b_o d^2}$ | 0.892 | ~0.3-0.7 | $\dfrac{4ab\beta}{d}$ | $2b_o d$ | 0.5 < a/b < 2<br>a = 5-10 mm<br>$b_o$ = 2 mm<br>d = 1 mm |

Table 1 above shows a summary of some of the important features of the different small specimen creep tests.

An advantage obtained using the present invention is that it allows easily measureable deformations to be obtained related to relatively small equivalent strains when related to the corresponding uniaxial test. Hence, apart from the ease with which the experiments can be performed, stresses and temperatures can be chosen to be much closer to practical operating values. It is also noted that the deformations do not significantly affect the parameters $\eta$ and $\beta$, which enables accurate secondary creep properties to be easily obtained.

Figure 7:
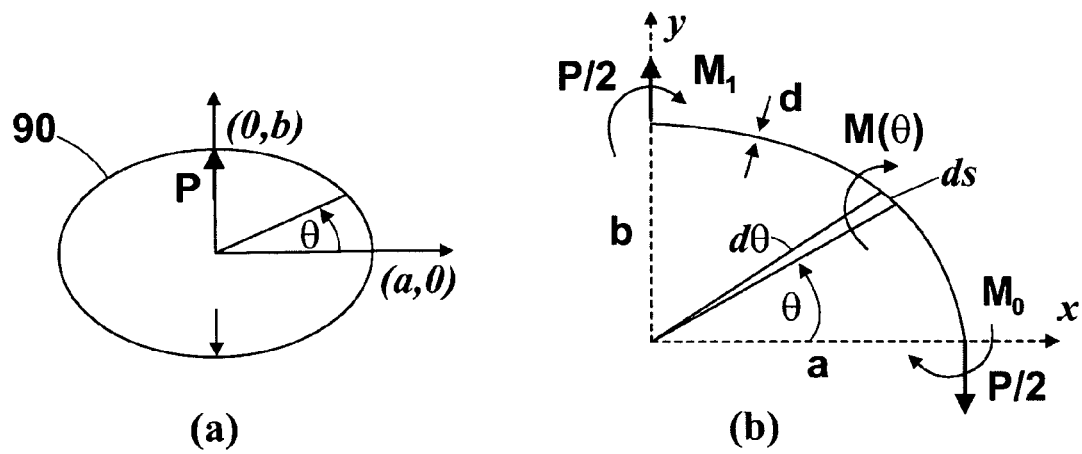
FIG. 7 shows an analytical model representation of the diametrically loaded ring in accordance with a preferred embodiment of the present invention.

FIGS. 6 and 7 show the elliptical ring 90, FIG. 7(a), and the free body diagram, FIG. 7(b), of a symmetric quadrant of the elliptical ring 90. A circular ring 100 is a special case of the elliptical ring 90, derived in which a/b=1.

A diametric force is applied to the sample 10 in order to deform the sample 10 over a period of time. Preferably or optionally the diametric force applied to the sample 10 is a single deformation mechanism which does not, to any significant extent locally deform the sample 10 at the point of application of the diametric force 50. As shown in FIG. 7(a) a load is applied at either point P 50, the force 50 applied by the load deforms the sample 10 at a number of continuous points around the circumference of the sample 10 but no significant local deformation occurs at the point of application of the force 50.

Creep is defined as a high temperature progressive deformation at constant stress. "High temperature" is a relative term dependent upon the materials involved. The prior art states that in order to evaluate the creep in a material using the known specimen samples means that rather higher temperatures or stresses than those expected under operating conditions are required. In accordance with the present invention the use of the sample in this case the elliptical ring 90, allows stresses and temperatures to be chosen to be much closer to practical operating values of the materials from which the sample 10 was taken.

As will be shown in the following calculations a steady state time dependent deformation rate is calculated to determine a minimum creep strain rate. The minimum creep strain rate is dependent upon the relationship of the deformation of the sample 10 and the equivalent gauge length of the flexible small sample 10. The gauge length also allows easily measureable deformations to be obtained related to relatively small strains.

The following calculations for a sample 10 in this case the elliptical ring 90 show that the results obtained are comparable with those of known prior art small specimens. However, the sample 10 of the present invention (either the elliptical ring 90 or the circular ring 100) are easy to manufacture, compared with conventional samples 10. Also, because the samples 10 are designed to obtain creep strain rate data, i.e. not creep rupture data, the surface finish is not too critical and samples 10 may be made using, for example, a water jet cutting machine; such a machine is highly versatile and capable of being programmed to make much more complicated shapes than the elliptical rings 90 or circular rings 100 described above. It will be appreciated that the ring-like shape of the specimen could also be a closed ring or not. It could be a split ring, or a C-shape for example.

Figure 13:
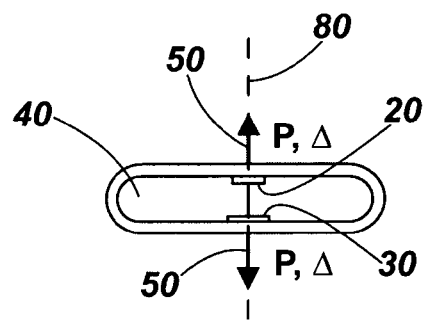
FIG. 13 shows a plan view of small specimen geometries in accordance with further embodiments of the present invention.
Figure 13:
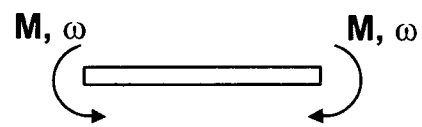
Figure 13:
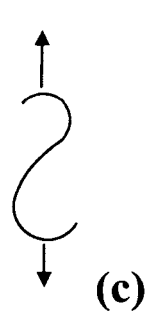
Figure 13:
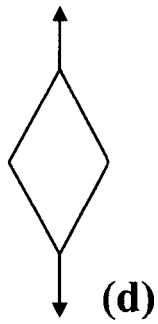
Figure 13:
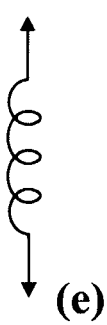
Figure 13:
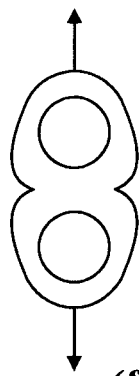
Figure 13:
Figure 13:
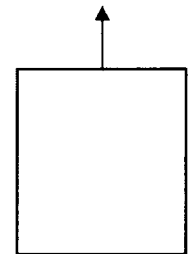
Figure 13:
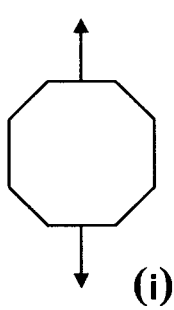
Figure 13:
Figure 13:
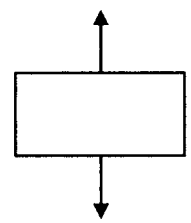

The loading system, experimental setup and alignment procedures used for the sample 10 are simple to operate. Temperature control is no more difficult than for other small sample 10 test types and because creep deformations are relatively large, the sensitivity is not significantly affected by the small thermal strains which occur due to the unavoidable temperature variations which occur within the test furnace. Elliptical geometries with a/b>1, and other similarly shaped specimens, such as that shown in FIG. 13(a), are capable of minimising the effects of small transverse deformations which occur during the tests. The most important aspect of the sample 10 design concept is the high EGL values which can be achieved. This allows easily measureable deformations to be obtained related to relatively small strains corresponding to the equivalent uniaxial test.

It will be appreciated that a very simple creep test is to hang a weight off one of the contact surfaces and support the specimen (and the weight) off the other contact surface. One contact surface would then be a weight bearing surface (or an applied force surface) and the other contact surface is a reaction force surface. If the surfaces are concave in shape on the inside of the areas where the weight is contacted with the specimen and where a reaction support contacts the specimen, then the sample, weight, and reaction surface could all be self-aligning or self-centering: in that gravity could automatically line up the points at which the weight force is applied to the ring-like specimen and the point at which the force of the weight is reacted. This makes the creep test easy to use.

As will be shown the deformations do not significantly affect the parameters $\eta$ and $\beta$, which enables accurate secondary creep properties to be easily obtained.

The stationary state solution for the deformation of a structure made from a nonlinear material obeying a time-dependent model of the Norton form $$\dot{\epsilon}^c = B|\sigma|^n \text{sign}(\sigma) \tag{5}$$

is of exactly the same form as that for a time-independent nonlinear material obeying a constitutive equation of the form $$\epsilon = B|\sigma|^n \text{sign}(\sigma) \tag{6}$$

The only difference in the two solutions is that the expression obtained for displacement using a material model described by equation (6) would be replaced by an expression for displacement rate using a material model described by equation (5).

In further calculations, shown below, the derived relationship between the bending moment and stress in a beam is, i.e.

$$\sigma = \frac{M|y|^{\frac{1}{n}}}{I_n} \text{sign}(y)$$

where $$I_n = \int_A y^{1+\frac{1}{n}} dA$$

Using the principles of virtual complimentary work and stationary complimentary energy, it can be shown that $$u_i = \frac{\partial U^*}{\partial P_i}, i = 1, 2, \ldots, k \quad (7)$$

where $u_i$ are the displacements at the point of application and in the directions of a set of "k" loads, $P_i$ (i=1, 2 ... k). For the case of a beam in bending, U* is given by:

$$U^* = \frac{4B}{(n+1)(I_n)^n} \int |M|^{n+1} ds \quad (8)$$

where $$M = \frac{P}{2}a(1-\cos\theta) - M_o \quad (9)$$

$$ds = \sqrt{a^2\sin^2\theta + b^2\cos^2\theta}\, d\theta \quad (10)$$

and $$\frac{x^2}{a^2} + \frac{y^2}{b^2} = 1 (x = a\cos\theta \text{ and } y = b\sin\theta)$$

When M=0, θ=θ', say, where $$\cos\theta' = \left(1 - \frac{2M_o}{Pa}\right) \quad (11)$$

Using equation (7), $$\frac{\partial U^*}{\partial M_o} = 0 \quad (12a)$$

$$\frac{\partial U^*}{\partial P} = \Delta \quad (12b)$$

Using equations (8) with (11) and 12(a) gives $$0 = \int_0^{\theta'} (\cos\theta - \cos\theta')^n \sqrt{\left(\frac{a}{b}\right)^2 \sin^2\theta + \cos^2\theta}\, d\theta - \int_{\theta'}^{\frac{\pi}{2}} (\cos\theta' - \cos\theta)^n \sqrt{\left(\frac{a}{b}\right)^2 \sin^2\theta + \cos^2\theta}\, d\theta; \quad (13)$$

Figure 8:
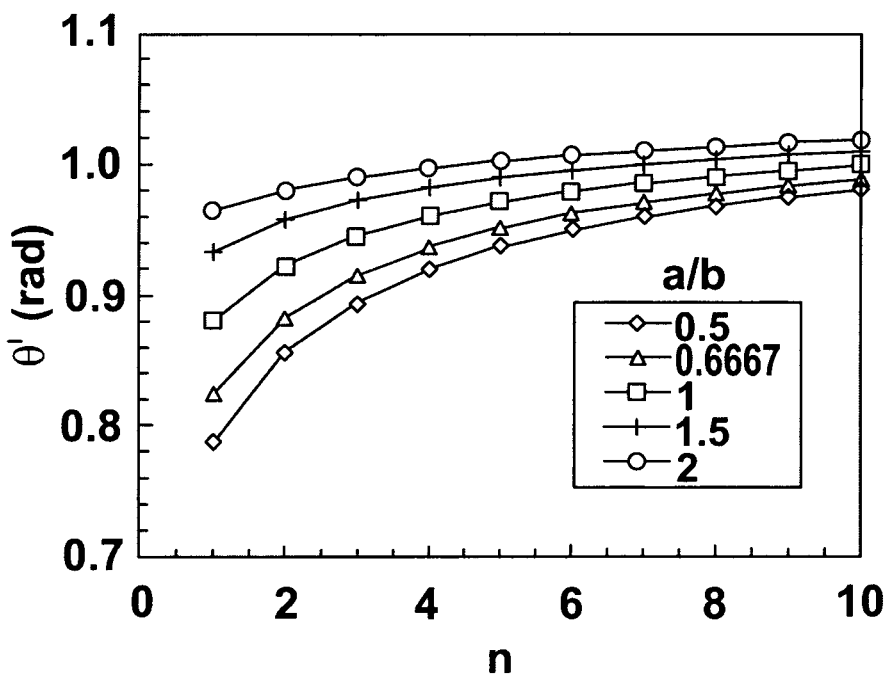
FIG. 8 shows a graph of the variations of $\theta'$ with n for a range of a/b in accordance with a preferred embodiment of the present invention.

Equation (13) can be solved numerically to obtain θ' for any particular value of n and a/b, see FIG. 8. The right hand side of equation (13) is defined as $\text{Int}_1$ (n, a/b).

Using equations (8) with (11) and 12(b) gives $$\Delta = \frac{2Bab}{(I_n)^n}\left(\frac{Pa}{2}\right)^n \quad (14)$$

$$\left\{-\int_0^{\theta'} (\cos\theta - \cos\theta')^n (1-\cos\theta)\sqrt{\left(\frac{a}{b}\right)^2 \sin^2\theta + \cos^2\theta}\, d\theta + \int_{\theta'}^{\frac{\pi}{2}} (\cos\theta' - \cos\theta)^n (1-\cos\theta)\sqrt{\left(\frac{a}{b}\right)^2 \sin^2\theta + \cos^2\theta}\, d\theta\right\}$$

The term inside the { ... } brackets in equation (14) is a function of n and a/b; this is defined as $\text{Int}_2$ (n, a/b).

Therefore, equation (14) can be simplified and converted to a stationary state creep solution as:—

$$\dot{\Delta} = \frac{2Bab}{(I_n)^n}\left(\frac{Pa}{2}\right)^n \text{Int}_2\left(n, \frac{a}{b}\right) \quad (15)$$

In particular, for a rectangular cross-section beam, i.e.

$$I_n = \frac{2n}{2n+1}b_o\left(\frac{d}{2}\right)^{\frac{2n+1}{n}} \quad (16)$$

then $$\dot{\Delta} = \left(\frac{2n+1}{n}\right)^n \text{Int}_2\left(n, \frac{a}{b}\right)\frac{4ab}{d}B\left(\frac{Pa}{b_o d^2}\right)^n$$

Using MacKenzie's method for determining reference stresses, $$\dot{\Delta} = \left(\frac{2n+1}{n}\right)^n \frac{\text{Int}_2\left(n, \frac{a}{b}\right)}{\alpha^n}\frac{4ab}{d}B\left(\alpha\frac{Pa}{b_o d^2}\right)^n \quad (17)$$

Choosing the value of α(=η) which makes $$\left(\frac{2n+1}{n}\right)^n \frac{\text{Int}_2\left(n, \frac{a}{b}\right)}{\alpha^n}$$

independent of n leads to $$\dot{\Delta} = \beta\left(\frac{4ab}{d}\right)B(\sigma_{ref})^n \quad (18)$$

where β is constant for a given a/b, $$\beta = \left(\frac{2n+1}{n}\right)^n \frac{\text{Int}_2\left(n, \frac{a}{b}\right)}{\eta^n} \text{ and} \quad (19)$$

$$\sigma_{ref} = \eta\frac{Pa}{b_o d^2}$$

Re-arranging equation (18) gives $$\dot{\varepsilon}^c(\sigma_{ref}) = \frac{d}{4ab\beta}\dot{\Delta} \qquad (20)$$

Equations (19) and (20) give the equivalent uniaxial stress and EGL for an elliptical specimen.

For the special case of a circular ring, i.e. $a=b=R_s$, equation (20) becomes:—

$$\dot{\varepsilon}^c(\sigma_{ref}) = \frac{d}{4R^2\beta}\dot{\Delta} \qquad (21)$$

where $$\sigma_{ref} = \eta\frac{PR}{b_o d^2} \qquad (22)$$

Figure 9:
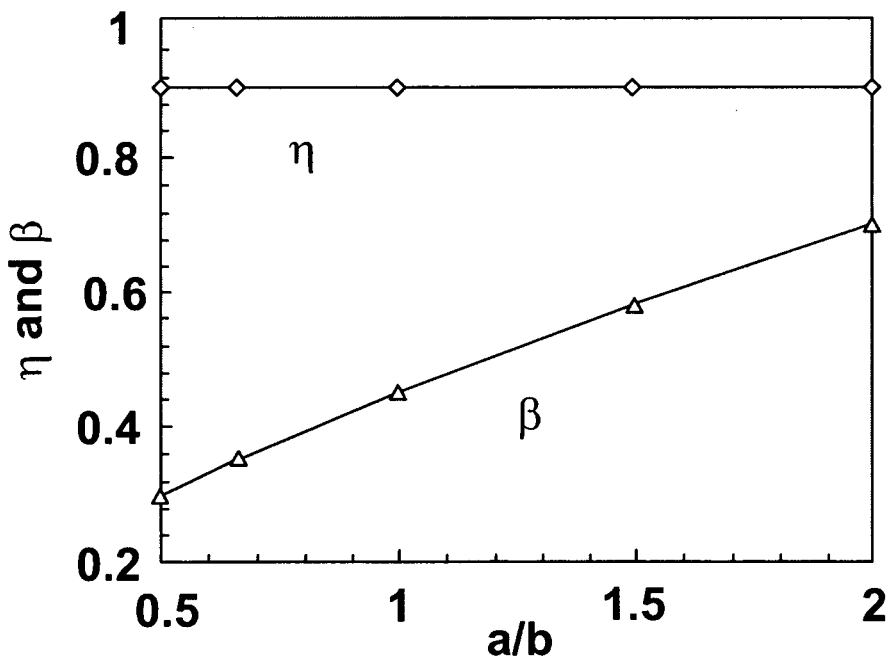
FIG. 9 shows a graph of the variations of the $\eta$ and $\beta$ parameters with a/b in accordance with a preferred embodiment of the present invention.

The variations of $\eta$ and $\beta$-values with a/b are shown in FIG. 9. The relevant results are added to those in Table 1 for comparison with those of the commonly used small specimens.

For some typical dimensions, it can be seen (Table 1) that the test section area (beam cross-section) is about 5-10 mm² which is good by comparison with the other specimens. The EGL for the circular ring is approximately 32 mm for R=6 mm and d=2 mm or 64 mm for R=6 mm and d=1 mm. For an elliptical ring with a/b=2 and with a=8 mm, b=4 mm and d=1 mm, say, the EGL is about 90 mm. It is clear that these EGL values are significantly larger than the equivalent gauge length values applicable to commonly used small specimen types. The dimension range of the specimens can be chosen to match the load capacity of the test machines to be used and the EGL required. In order to make the specimens "small", 2R≤10 mm, d≈1 mm and $b_o$≈2 mm may be used.

An approximate reference stress can be obtained from knowledge of the limit load of a structure. Using this approach it can be shown that $$\sigma_{ref} \approx \frac{P}{P_L}\sigma_y \qquad (23)$$

and $$EGL \approx \frac{\Delta^e}{(\sigma_{ref}/E)}. \qquad (24)$$

An approximate limit load for a circular ring is derived, i.e.

$$P_L \approx \frac{b_o d^2}{R}\sigma_y \qquad (25)$$

Hence, using equations (23) and (25), $$\sigma_{ref} \approx \frac{PR}{b_o d^2} \qquad (26)$$

The accurate theoretical solution gives $$\sigma_{ref} = \eta\sigma_{nom} = 0.892\frac{PR}{b_o d^2}$$

Hence, the approximate, limit load, reference stress is about 10% higher than the more accurate value. Also, using the approximate reference stress, equation (26), in equation (24), together with the elastic solution for a diametrically loaded circular ring, i.e.

$$\Delta^e = \frac{PR^3}{4EI}\frac{(\pi^2-8)}{\pi} \qquad (27)$$

gives:—

$$EGL \approx \frac{R^2}{d}\frac{3(\pi^2-8)}{\pi} \approx 1.788\frac{R^2}{d} \qquad (28)$$

The accurate theoretical solution (Equation (20)) gives $$EGL = 1.792\frac{R^2}{d}$$

Hence, the approximate EGL value is about 0.5% lower than the more accurate value.

Figure 10:
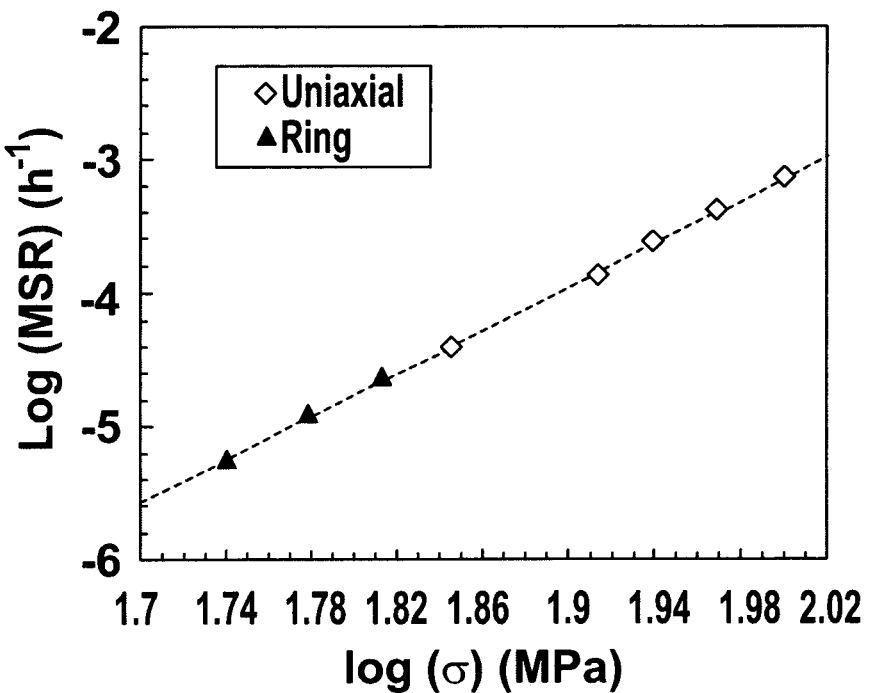
FIG. 10 shows a comparison graph for P91 steel at 650° C. for both a uniaxial specimen and a ring specimen in accordance with a preferred embodiment of the present invention.

The data shown in FIG. 1 was obtained using conventional creep specimens (using the specimen type shown in FIG. 2 with GL=50 mm and $d_{GL}$=10 mm), for a P91 steel at 650° C. The creep strain rates obtained from the secondary creep regions are shown plotted against the stresses in FIG. 10.

Figure 11:
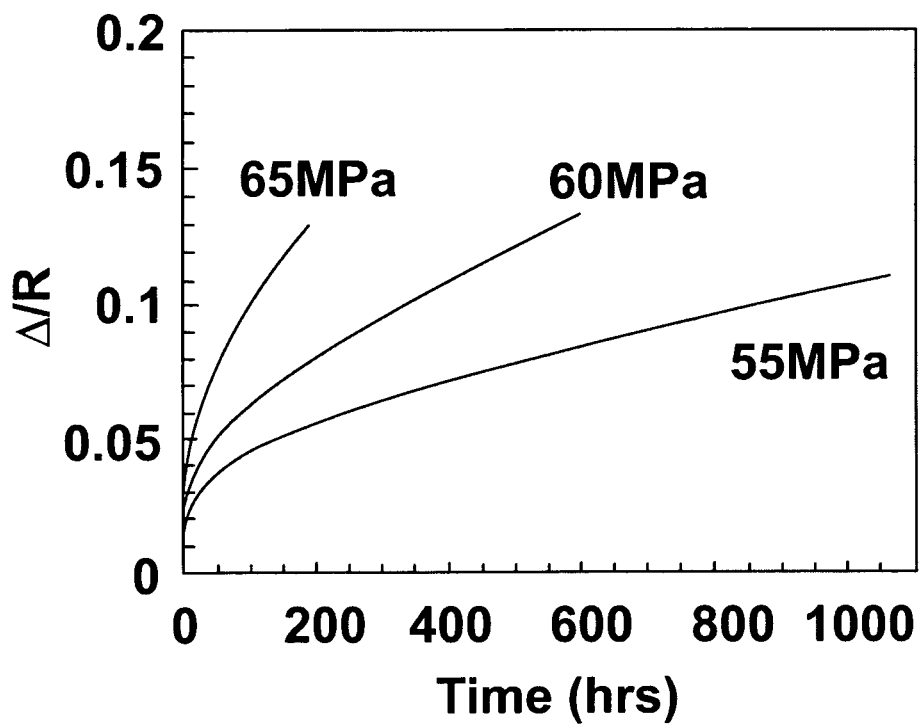
FIG. 11 shows a graph of the displacement versus time for a diametrically loaded P91 steel ring specimen at 650° C. in accordance with a preferred embodiment of the present invention.

The same material was used to manufacture circular rings (a/b=1) with R/d=5. These specimens were tested in diametrical tension, at 650° C., with loads corresponding to uniaxial stresses (obtained using Equation (22)) of 55, 60 and 65 MPa; the displacement versus time data for these tests are shown in FIG. 11. The minimum displacement rates were converted into equivalent uniaxial strain rates using equation (21). This data is included in FIG. 10 for comparison with the corresponding uniaxial data.

In order to further improve the accuracy of the results obtained from the ring test data the slight ellipticity which develops during testing can be corrected for by using the instantaneous a and b values and deformation rates in equations (19) and (20). These slight ellipticity errors which develop during testing of circular rings (as a result of creep deformation) can be practically eliminated by starting with an elliptical specimen (a/b=2, say) for which the loadline displacement is accompanied by a relatively small transverse reduction of the major axis of the elliptical ring, compared with that which occurs for a circular ring.

Figure 12:
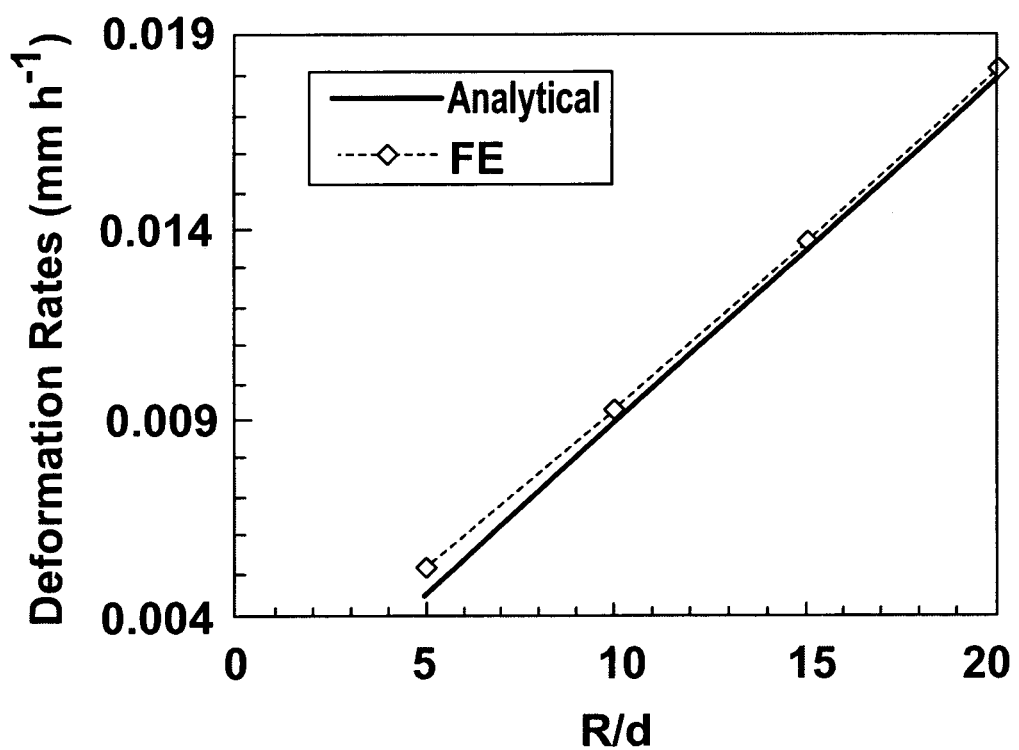
FIG. 12 shows a graph of the variations of FE steady-state load-line deformation rates with R/d for a specific load magnitude and material property values compared with predictions obtained from the corresponding analytical solutions in accordance with a preferred embodiment of the present invention.

In order to further verify the technique, FE analyses (under plane stress conditions) were performed for a circular ring, with R=10 and $b_o$=1, for a number of R/d values. The variations of FE steady-state load-line deformation rates with R/d, for a specific load magnitude and material property values, are compared with predictions obtained from the corresponding analytical solutions, in FIG. 12. It can be seen that the deformation rates obtained from both methods are practically the same when R/d≥15. When R/d=5, the load-line deformation rate obtained from the FE analysis is about 15% higher than that obtained from the analytical solution. This indicates that when the R/d ratio is small, more accurate η and β values may need to be obtained, using FE analyses, in order to take account the "shear" contribution.

Relationship Between Bending Stress Distribution and Bending Moment

The axial strain and the bending moment of a beam under pure bending conditions are:—

$$\varepsilon = \frac{y}{R_o} \tag{A1-1}$$

$$M = \int_A y\sigma(y)\,dA \tag{A1-2}$$

where $R_o$ is the radius of curvature. Assume a non-linear power law material behaviour model as follows: —

$$\epsilon = B|\sigma|^n \text{sign}(\sigma) \tag{A1-3}$$

which leads to $$\sigma = \frac{M|y|^{\frac{1}{n}}}{I_n}\text{sign}(y) \tag{A1-4}$$

where $$I_n = \int_A |y|^{1+\frac{1}{n}}\,dA \tag{A1-5}$$

Complimentary Strain Energy for Beam-Type Structures

A non-linear power law material behaviour model is given by $$\epsilon = B|\sigma|^n \text{Sign}(\sigma) \tag{A1-3}$$

Figure 14:
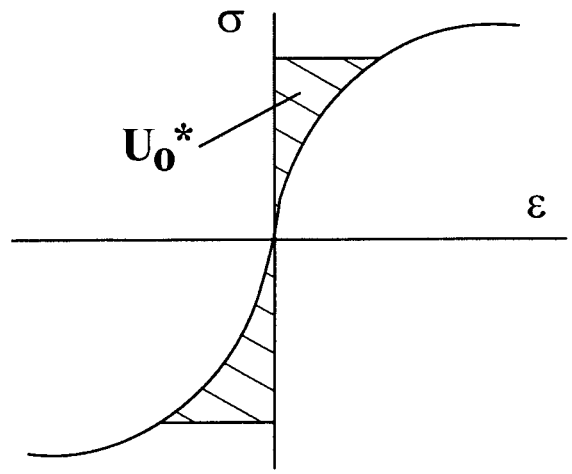
FIG. 14 shows a graph of the complimentary strain energy density for beam type structures of a ring in accordance with the present invention.

The complimentary strain energy density (FIG. 14) is $$U_o^* = \int \varepsilon\,d\sigma = \frac{B}{n+1}|\sigma|^{n+1} \tag{A2-2}$$

Therefore, for the ring, assumed to be comprised of beam-type structures (four quadrants), the total complimentary strain energy of the structure is given by:—

$$U^* = \int_V U_o^*\,dV = \frac{4B}{(n+1)I_n^n}\int_S |M|^{n+1}\,ds \tag{A2-3}$$

Use of Complimentary Strain Energy for a Diametrically Loaded Elliptical Ring to Obtain the Radial Deformation The geometry and loading are shown in FIGS. 7(*a*) and 7(*b*).

For an ellipse, FIG. 7(*a*), $$\frac{x^2}{a^2} + \frac{y^2}{b^2} = 1$$

x=a cos θ
y=b sin θ
$(ds)^2=(dx)^2+(dy)^2$, therefore, $$ds = \sqrt{a^2\sin^2\theta + b^2\cos^2\theta}\,d\theta \tag{A3-1}$$

The bending moments in the ring, FIG. 7(*b*), are:—

$$M_1 = M_o + \frac{Pa}{2} \tag{A3-2}$$

$$M = \frac{P}{2}a(1-\cos\theta) - M_o$$

When $M = 0$, \hfill (A3-3)

$$\cos\theta' = \left(1 - \frac{2M_o}{Pa}\right)$$

For the case of pure bending, for a material obeying a power relationship of the form given by equation A1-3, the complimentary strain energy density is given by:—

$$U_o^* = \frac{B}{n+1}\left(\frac{|M|\cdot |y|^{\frac{1}{n}}}{I_n}\right)^{n+1} \tag{A3-4}$$

Therefore, for a beam with uniform cross-sectional area, $$U^* = \int_V U_o^*\,dV = \frac{B}{(n+1)(I_n)^n}\int_S |M|^{n+1}\,ds \tag{A3-5}$$

For the elliptical ring, $$U^* = \frac{4B}{(n+1)(I_n)^n}\int |M|^{n+1}\,ds \tag{A3-6}$$

$$= \frac{4B}{(n+1)(I_n)^n}\left\{\int_0^{\theta'}\left(M_o - \frac{Pa}{2}(1-\cos\theta)\right)^{n+1}\,ds + \int_{\theta'}^{\frac{\pi}{2}}\left(\frac{Pa}{2}(1-\cos\theta)\right)^{n+1}\,ds\right\}$$

Using equations 12(a) and 11, the following relationship is obtained:—

$$0 = \int_0^{\theta'}(\cos\theta - \cos\theta')^n\sqrt{\left(\frac{a}{b}\right)^2\sin^2\theta + \cos^2\theta}\,d\theta - \tag{A3-7}$$

$$\int_0^{\frac{\pi}{2}}(\cos\theta' - \cos\theta)^n\sqrt{\left(\frac{a}{b}\right)^2\sin^2\theta + \cos^2\theta}\,d\theta$$

$$= Int_1\left(n, \frac{a}{b}\right)$$

from which the θ'-value, which is dependent on n and a/b, can be obtained, see FIG. 8.

Also, using equations 12(b) and 11, the load point deformation rate can be obtained:—

$$\dot{\Delta} = \frac{2Bab}{(I_n)^n}\left(\frac{Pa}{2}\right)^n \tag{A3-8}$$

$$\left\{-\int_0^{\theta'}(\cos\theta - \cos\theta')^n(1-\cos\theta)\sqrt{\left(\frac{a}{b}\right)^2\sin^2\theta + \cos^2\theta}\,d\theta + \right.$$

-continued $$\int_{\theta'}^{\frac{\pi}{2}} (\cos\theta' - \cos\theta)^n (1-\cos\theta) \sqrt{\left(\frac{a}{b}\right)^2 \sin^2\theta + \cos^2\theta} \, d\theta \Bigg\}$$

Figure 15:
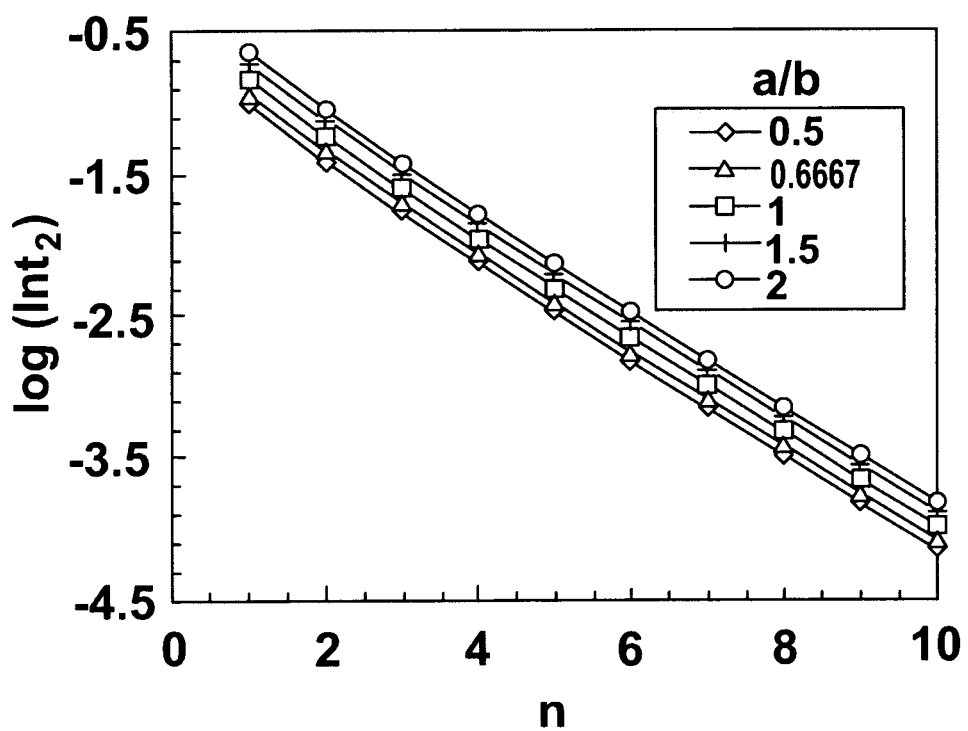
FIG. 15 shows a graph of variations of $Int_2$ with n for a range of a/b in accordance with the present invention.

The term inside the { ... } brackets in equation. (A3-8) is a function of n and a/b; see FIG. 15; this is defined as $Int_2$ (n, a/b). Therefore, equation (A3-8) becomes:

$$\dot{\Delta} = \frac{2Bab}{(I_n)^n} \left(\frac{Pa}{2}\right)^n Int_2\left(n, \frac{a}{b}\right) \quad (A3\text{-}9)$$

If $a = b(=R, \text{ say})$:- $\quad$ (A3-10)

$$Int_1(n) = \int_0^{\theta'} (\cos\theta - \cos\theta')^n d\theta - \int_0^{\frac{\pi}{2}} (\cos\theta' - \cos\theta)^n d\theta$$

$$Int_2(n) = -\int_0^{\theta'} (\cos\theta - \cos\theta')^n (1-\cos\theta) d\theta + \quad (A3\text{-}11)$$
$$\int_{\theta'}^{\frac{\pi}{2}} (\cos\theta' - \cos\theta)^n (1-\cos\theta) d\theta$$

Therefore $$\dot{\Delta} = \frac{2BR^2}{(I_n)^n} \left(\frac{PR}{2}\right)^n Int_2(n) \quad (A3\text{-}12)$$

Approximate Limit Load for the Circular Ring

FIG. 16 shows the load and deformation of the ring with fully plastic hinges at positions A, B, C and D. If γ is small, cos γ≈1 and sin γ≈γ, therefore, $$\cos(45° + \gamma) = \frac{1}{\sqrt{2}} - \frac{1}{\sqrt{2}}\gamma = \frac{R - \Delta/2}{\sqrt{2}\,R} \quad (A4\text{-}1)$$

which gives $$\gamma = \Delta/2R$$

Work done by $P_L$ (the limit load) is dissipated in the formation of the plastic "hinges" at A, B, C and D, therefore, $$P_L \Delta \approx 4\left(M_L \frac{2\gamma}{R}\right) \quad (A4\text{-}2)$$

From equations (A4-2) and (A4-1), $$P_L \approx 4\frac{M_L}{R} \quad (A4\text{-}3)$$

For a rectangular cross-sectional beam, $$M_L = \frac{b_o d^2}{4}\sigma_y$$

$$P_L \approx \frac{b_o d^2}{R}\sigma_y$$

Process for the Derivation of Equivalent Gauge Length (EGL)

For a conventional uniaxial creep test, the creep strain at a time is usually measured from the deformation of the gauge length (GL). If the gauge length elongation is Δ and the elastic portion is neglected, $$\varepsilon^c \approx \frac{\Delta}{GL} \quad (A5\text{-}1)$$

For non-conventional small creep test specimens, an equivalent gauge length (EGL) could be defined, if the measured creep deformation can be related to an equivalent uniaxial creep strain, in the same form as that of Equation (A5-1), i.e.

$$\varepsilon^c \approx \frac{\Delta^c}{EGL} \quad (A5\text{-}2)$$

The EGL is related to the dimensions of the specimen and in some cases may be related to the time-dependent deformation of the test specimen. The creep strain and creep deformation given in Equation (A5-2) may be presented in a form of the reference stress, $\sigma_R$, i.e.

$$\Delta^c \approx D\epsilon^c(\sigma_R) \quad (A5\text{-}3)$$

In which D is the reference multiplier, which is in fact the EGL for the test. In some cases, the geometric changes, due to the specimen creep deformation with time, are small (e.g. for impression creep test), and in such cases, the effects of geometric changes on D (EGL) can be neglected for simplicity.

For some specimen types, such as the ring or elliptical specimens, creep deformation $\Delta^c$ can be obtained from analytical solutions, for example, using the principles of virtual complimentary work and stationary total complimentary energy. Therefore, if a reference stress approach is used, analytical solutions for the reference stress, $\sigma_R$, and the reference multiplier, D, may be obtained. In more general situations when $\Delta^c$ cannot be obtained analytically, a numerical procedure, using, for example, the finite element analysis, can be used to determine the reference stress, $\sigma_R$, which is related to the applied load, and the reference multiplier, D (EGL), which is a function of specimen dimensions.

Although the present invention has been illustrated and described with respect to exemplary embodiment thereof, it should be understood by those skilled in the art that the foregoing and various other changes, omission and additions may be made therein and thereto, without departing from the scope of the invention. Therefore the present invention should not be understood as limited to the specific embodiment set out above but to include all possible embodiments which can be embodied within a scope encompassed and equivalent thereof with respect to the features set out in the appended claims.

The invention claimed is:

1. A method for testing the mechanical properties of a specimen having a first contact surface and a second contact surface spaced apart and opposing the first contact surface, the method comprising:
    applying a force to the first contact surface or the second contact surface of the specimen to deform the specimen force over a period of time and determining a response of the specimen to the force over time; and
    defining a spatial distance between the contact surfaces such that the specimen's equivalent gauge length is greater than the distance between the contact surfaces;
    wherein the force is applied by hanging a weight from either the first contact surface or the second contact surface, and the contact surface which does not have the force applied to it is secured to an apparatus for testing mechanical properties of the specimen, wherein when the force is applied to the first contact surface or the second contact surface an equal and opposite reactive force is applied to the other contact surface, and wherein the first contact surface and/or the second contact surface is shaped so as to self-align or self-center a specimen within the apparatus for testing the mechanical properties of the specimen.

2. The method according to claim 1, further comprising obtaining a sample of material from an object to be tested and forming the specimen from the sample.

3. The method according to claim 2, further comprising operating on the sample with machine tools to form the specimen.

4. The method according to claim 2, further comprising forming a ring-like shaped specimen from the sample.

5. The method according to claim 1, wherein the first contact surface is either a concave surface or convex surface, and wherein the second contact surface is also either a concave surface or a convex surface.

6. The method according to claim 5, wherein the specimen is symmetrical about a line joining the contact surfaces.

7. The method according to claim 5, wherein the specimen comprises a ring-like shape.

8. The method according to claim 7, wherein the specimen comprises an elliptical shape or a circular shape.

9. The method according to claim 7, wherein the specimen has a flattened elliptical shape having two opposed generally parallel sides and at least one, curved region linking the parallel sides.

10. The method according to claim 1, wherein the forces applied to the contact surfaces force the surfaces toward each other.

11. The method according to claim 1, wherein the forces applied to the contact surfaces force the surfaces away from each other.

12. The method according to claim 1, wherein the forces applied to the contact surfaces is a diametric force which causes the contact surfaces to deform diametrically as a result of the forces being applied to at least a point on the contact surfaces.

13. The method according to claim 12, wherein the diametric force can be either a tension force or a compression force applied to the contact surfaces.

14. The method according to claim 1, wherein the equivalent gauge length of the specimen is greater than the distance between the contact surfaces.

15. The method according to claim 14, wherein the equivalent gauge length of the specimen is greater than or equal to 20 mm.

16. The method according to claim 14, wherein the equivalent gauge length of the specimen is at least two times the distance between the contact surfaces.

17. The method according to claim 1, further comprising heating the specimen to a temperature substantially identical to an operating temperature which the specimen would operate at.

18. The method according to claim 1, wherein the specimen is formed from a sample by a sample scooping technique.

19. The method according to claim 1, wherein testing the mechanical properties of the specimen comprises creep testing the specimen.

20. A specimen for testing the mechanical properties of a material, the specimen comprising:

a first contact surface;
a second contact surface;
wherein the second contact surface opposes the first contact surface and defines an opening in between each surface;
wherein the specimen defines a spatial distance between the contact surfaces such that the specimen's equivalent gauge length is greater than the distance between the contact surfaces;
wherein a force is applied by hanging a weight from either the first contact surface or the second contact surface and the other contact surface which does not have the force applied to it is secured to an apparatus for testing the mechanical properties of the specimen;
wherein when the force is applied to the first contact surface or the second contact surface an equal and opposite reactive force is applied to the other contact surface; and
wherein the first contact surface and/or the second contact surface is shaped so as to self-align or self-center a specimen within the apparatus for testing the mechanical properties of the specimen.

21. The specimen according to claim 20, wherein the first contact surface is either a concave surface or convex surface, and wherein the second contact surface is also either a concave surface or a convex surface.

22. The specimen according to claim 20, wherein the specimen is symmetrical about a line joining the contact surfaces.

23. The specimen according to claim 20, wherein the specimen comprises a ring-like shape.

24. The specimen according to claim 23, wherein the specimen comprises an elliptical shape, a flattened elliptical shape, a circular shape, a split-ring shape, or a C-shape.

25. The specimen according to claim 20, wherein the specimen is formed from a sample of the material by a sample scooping technique.

26. The specimen according to claim 20, wherein the equivalent gauge length of the specimen is greater than the distance between the contact surfaces.

27. The specimen according to claim 26, wherein the equivalent gauge length of the specimen is greater than or equal to 20 mm.

28. The specimen according to claim 26, wherein the equivalent gauge length of the specimen is at least two times the distance between the contact surfaces.

29. The specimen according to claim 20, wherein testing the mechanical properties of the specimen comprises creep testing the specimen.

30. A process for producing a product from a production plant comprising:

operating the plant to produce the product;
checking the expected operational life of a component of the plant by:
  (i) obtaining a sample of the material of a component of the plant, and forming from the sample a specimen comprising:
    a first contact surface;
    a second contact surface;
    wherein the second contact surface opposes the first contact surface and defines an opening in between each surface; and
    wherein the specimen defines a spatial distance between the contact surfaces such that the specimen's equivalent gauge length of the specimen is greater than the distance between the contact surfaces; and
  (ii) performing a test on the specimen using the method according to claim 1;

determining that the component has a remaining safe operational life; and continuing to produce more product, using the component in the future.

31. The process according to claim 30, wherein the product is electricity and the plant is an electricity generating plant.

32. The method according to claim 9, wherein the specimen has a flattened elliptical shape having two opposed generally parallel sides and two curved regions linking the parallel sides.

33. The method according to claim 16, wherein the equivalent gauge length of the specimen is at least four times the distance between the contact surfaces.

34. The specimen according to claim 28, wherein the equivalent gauge length of the specimen is at least four times the distance between the contact surfaces.

* * * * *

UNITED STATES PATENT AND TRADEMARK OFFICE
CERTIFICATE OF CORRECTION

PATENT NO. : 8,578,784 B2
APPLICATION NO. : 13/130247
DATED : November 12, 2013
INVENTOR(S) : Thomas Horace Hyde and Wei Sun It is certified that error appears in the above-identified patent and that said Letters Patent is hereby corrected as shown below:

In the Claims:

Column 20, line 61, the text "force over a period of time" should be changed to -- over a period of time --.

Column 21, line 31, the text "at least one, curved" should be changed to -- at least one curved --.

Signed and Sealed this
Fourteenth Day of January, 2014

Michelle K. Lee
*Deputy Director of the United States Patent and Trademark Office*